United States Patent [19]

Kienzle

[11] 4,455,311
[45] Jun. 19, 1984

[54] IMIDAZOQUINAZOLINE DERIVATIVES WHICH INHIBIT THE AGGREGATION OF BLOOD PLATELETS, INHIBIT GASTRIC SECRETION OR HAVE ACTIVITY ON THE CIRCULATORY SYSTEM

[75] Inventor: Frank Kienzle, Flüh, Switzerland

[73] Assignee: Hoffmann-La Roche Inc., Nutley, N.J.

[21] Appl. No.: 402,471

[22] Filed: Jul. 28, 1982

[30] Foreign Application Priority Data

Aug. 28, 1981 [CH] Switzerland ............ 5548/81
Jun. 17, 1982 [CH] Switzerland ............ 3744/82

[51] Int. Cl.$^3$ .............. A61K 31/505; C07D 487/04
[52] U.S. Cl. ................................ 424/251; 544/250
[58] Field of Search ............................ 424/251; 544/250

[56] References Cited

U.S. PATENT DOCUMENTS 4,256,748 3/1981 Chodnekar et al. ............ 424/251
4,390,540 6/1983 Chodnekar et al. ............ 424/251

FOREIGN PATENT DOCUMENTS 46267 2/1982 European Pat. Off.
29591 3/1981 Japan ................................ 544/250

Primary Examiner—Mary C. Lee
Assistant Examiner—Diana G. Rivers
Attorney, Agent, or Firm—Jon S. Saxe; Bernard S. Leon; William G. Isgro

[57] ABSTRACT

Imidazoquinazolines of the formula

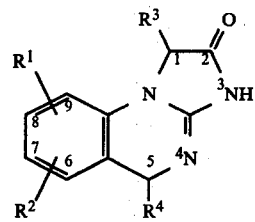

wherein one of $R^1$ or $R^2$ is hydrogen, chlorine, bromine, $C_{1-4}$-n-alkyl or $C_{1-4}$-n-alkoxy and the other is —N(R,R''), wherein R and R'' are $C_{1-4}$-n-alkyl or R and R'' taken together are tetramethylene or pentamethylene, and $R^3$ and $R^4$, independently, are hydrogen or methyl, their tautomers, when $R^3$ and/or $R^4$ are other than hydrogen, enantiomers thereof, as well as physiologically compatible acid addition salts of such compounds are described. The foregoing compounds inhibit the aggregation of blood platelets, inhibit gastric secretion or have activity on the circulatory system. Such compounds are prepared starting from the corresponding 4-benzylimidazo[1,2-a]quinazolin-2(1H)-ones in which the benzyl group is optionally substituted in the ortho- or para-position by $C_{1-4}$-alkyl or $C_{1-4}$-alkoxy.

14 Claims, No Drawings

IMIDAZOQUINAZOLINE DERIVATIVES WHICH INHIBIT THE AGGREGATION OF BLOOD PLATELETS, INHIBIT GASTRIC SECRETION OR HAVE ACTIVITY ON THE CIRCULATORY SYSTEM

BRIEF SUMMARY OF THE INVENTION

The invention relates to imidazoquinolines of the formula

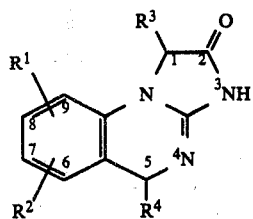

wherein one of $R^1$ or $R^2$ is hydrogen, chlorine, bromine, $C_{1-4}$-n-alkyl or $C_{1-4}$-n-alkoxy and the other is —N(R,R''), wherein R and R'' are $C_{1-4}$-n-alkyl or R and R'' taken together are tetramethylene or pentamethylene and $R^3$ and $R^4$, independently, are hydrogen or methyl, their tautomers, when $R^3$ and/or $R^4$ are other than hydrogen, enantiomers thereof, as well as physiologically compatible acid addition salts of such compounds. The foregoing compounds inhibit the aggregation of the blood platelets, inhibit gastric secretion or have activity on the circulatory system. The compounds of formula I, their tautomers, respective enantiomers, or salts are prepared starting from the corresponding 4-benzylimidazo[1,2-a]quinazolin-2(1H)-ones in which the benzyl group is optionally substituted in the ortho- or para-position by $C_{1-4}$-alkyl or $C_{1-4}$-alkoxy.

DETAILED DESCRIPTION OF THE INVENTION

The invention relates to imidazoquinazolines of the formula

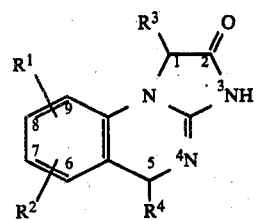

wherein one of $R^1$ or $R^2$ is hydrogen, chlorine, bromine, $C_{1-4}$-n-alkyl or $C_{1-4}$-n-alkoxy and the other is —N(R,R''), wherein R and R'' are $C_{1-4}$n-alkyl or R and R'' taken together are tetramethylene or pentamethylene and $R^3$ and $R^4$, independently, are hydrogen or methyl, their tautomers, when $R^3$ and/or $R^4$ are other than hydrogen, enantiomers thereof, as well as physiologically compatible acid addition salts of such compounds.

The compounds of formula I, their tautomers, enantiomers and salts thereof, are distinguished by valuable pharmacodynamic activities.

The invention also relates to the preparation of the referred to compounds, medicaments containing a compound of formula I, a tautomer thereof or, an enantiomer thereof, a pharmaceutically acceptable salt thereof and to the preparation of such medicaments as well as the use of compounds of formula I, their tautomers, enantiomers, or of pharmaceutically acceptable salts thereof in the control or prevention of illnesses.

As used herein, the term "$C_{1-4}$-n-alkyl" denotes methyl, ethyl and the straight-chain groups propyl and butyl, and the term "$C_{1-4}$-n-alkoxy" denotes alkoxy groups corresponding to the said alkyl groups.

Preferred among the compounds of formula I are those in which the group —N(R,R'') is located in the 6- or 7-position, especially in the 6-position; those in which R and R'' are $C_{1-4}$-n-alkyl, especially methyl; and finally those in which $R^3$ and $R^4$ are hydrogen.

Exemplary of preferred compounds are:

7-Dimethylamino-4,5-dihydroimidazo[1,2-a]quinazolin-2(1H)-one, its tautomers, as well as acid addition salts thereof.

Examples of physiologically or pharmaceutically compatible acid addition salts are mineral acid salts, especially, hydrochlorides, hydrobromides, sulfates and phosphates; salts with organic sulfonic acids, for example, alkylsulfonates or arylsulfonates; and carboxylic acid salts such as acetates, fumarates, oxalates and citrates.

The compounds of formula I can exist in various tautomeric forms. Therefore, the invention is not limited to compounds of formula I depicted earlier, but also includes their tautomers, for example, those of the formulas

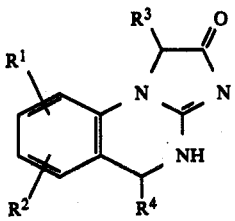

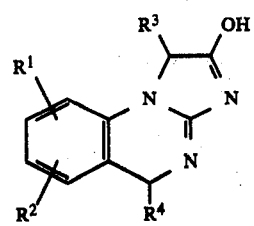

wherein $R^1$-$R^4$ are previously described.

The compounds of formula I and their tautomers in which $R^3$ and/or $R^4$ are/is different from hydrogen can, moreover, exist in the form of racemates or in an optically active form, all of these also form part of the invention.

The compounds of formula I and their tautomers, as well as the salts of such compounds can be prepared in accordance with the invention by reacting a compound of the formula

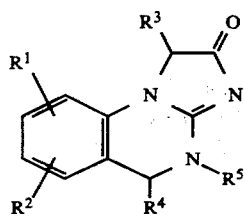

wherein $R^1$–$R^4$ are as previously described and $R^5$ is a benzyl group optionally ring-substituted in the ortho- or para-position by $C_{1-4}$-alkyl or $C_{1-4}$-alkoxy, with an acid, if desired chlorinating or brominating a resulting compound of formula I in which one of $R^1$ or $R^2$ is hydrogen, and isolating a resulting compound of formula I or a tautomer thereof in this form or in the form of a physiologically compatible acid addition salt.

A mineral acid such as orthophosphoric acid is conveninetly used as the acid. The reaction can be carried out at a temperature in the range of from room temperature to 170° C., preferably in the range of from 100° to 150° C., preferably in the presence of anisole.

The optional chlorination or bromination is conveniently carried out by reacting a compound of formula I in which one of $R^1$ or $R^2$ is hydrogen at a temperature in the range of from about 0° to 50° C., preferably at room temperature, in glacial acetic acid with chlorine or bromine, optionally in the presence of a catalyst such as ferric chloride.

The compounds of formula II can be prepared by reacting a compound of the formula

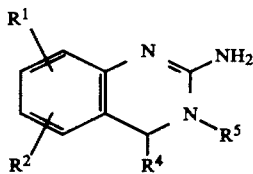

with an ester of the formula

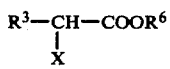

wherein $R^1$–$R^5$ are as previously described, $R^6$ is $C_{1-4}$-alkyl and X is chlorine, bromine or iodine, preferably iodine, conveniently in an organic solvent such as dimethylformamide or acetonitrile, at a temperature up to the reflux temperature of the reaction mixture, preferably in the presence of an inorganic base such as potassium carbonate.

The compounds of formula III can be prepared according to the Reaction Scheme which follows in which $R^1$–$R^5$ are as previously described in analogy to the process for the preparation of 3-substituted-2-amino-3,4-dihydroquinazoline derivatives starting from 2-nitrobenzyl chlorides described in Chem.Pharm.Bull 28 (1980) 1357–1364:

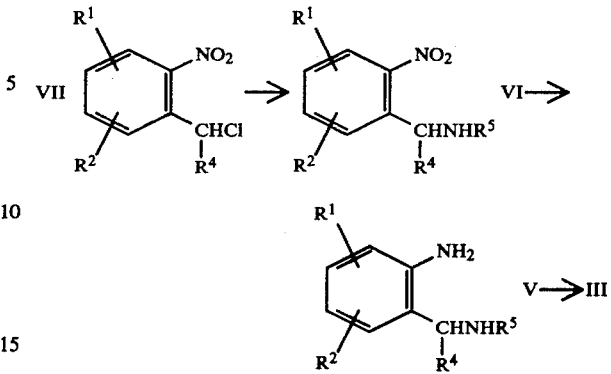

In this reaction the corresponding bromides can be used in place of the chlorides of formula VII. Such chlorides and bromides can be prepared, for example, in analogy to the preparation of α-chloro-N,N-dimethyl-4-nitrotoluidine described in Example 1 hereinafter by reducing the corresponding 2-nitrobenzoic acids and chlorinating or brominating the thus-obtained 2-nitrobenzyl alcohols.

The 2-nitrobenzoic acids are known or can be prepared, for example, in analogy to the preparation of 5-dimethylamino-2-nitrobenzoic acid which is described in U.S. Pat. No. 4,011,323.

The optically active compounds of formula I can be prepared from correspondingly substituted optically active starting materials of formulae IV and VII.

The compounds of formula I, their tautomers, when $R^3$ and/or $R^4$ are other than hydrogen, enantiomers thereof and physiologically compatible salts of such compounds can be used as medicaments. For example, foregoing compounds inhibit the aggregation of the blood platelets and can therefore be used for the prevention of thromboses. Further, they inhibit gastric acid secretion and can therefore be used for the treatment of gastric ulcers. Moreover, they are active on the circulatory system. Thus, for example, they exhibit positive inotropic activity without producing a substantial tachycardia and can be used for the treatment and prevention of cardiac insufficiency. An advantageous property common to the compounds provided by the invention is their high water solubility.

The compounds of formula I, their tautomers, when $R^3$ and/or $R^4$ are other than hydrogen, enantiomers thereof, and physiologically compatible salts of such compounds can be used as medicaments; for example, in the form of pharmaceutical preparations which contain them in admixture with an organic or inorganic inert carrier material which is suitable for enteral, percutaneous or parenteral administration such as, for example, water, gelatin, gum arabic, lactose, starch, magnesium stearate, talc, vegetable oils, polyalkylene glycols, and the like. The pharmaceutical preparations can be made up in solid form, for example, as tablets, dragées, suppositories or capsules, in semi-solid form, for example, as ointments, or in liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers. They can also contain other therapeutically active substances.

The oral and the parenteral administration of the compounds provided by the invention are preferred. For adults there come into consideration an oral daily dosage of 0.1 to 30 mg/kg and a parenteral daily dosage of 0.01 to 10 mg/kg. For the prevention of thromboses in adults a daily dosage of 1–10 mg is appropriate and for the treatment of cardiac insufficiency a daily dosage of 5–30 mg is appropriate, in each case taking into consideration the individual requirements of the warm-blooded animal and the form of administration.

The aggregation-inhibiting activity was demonstrated according to the aggregometer method of BORN [Nature 194, 927 (1962)] and MICHAL and BORN [Nature 231, 220 (1971)]. The maximum aggregation velocity was taken as the test parameter and the effective concentration ($EC_{50}$) was ascertained from dosage-activity curves.

Human platelet-rich plasma was obtained by centrifugation from citrated venous blood. The experiments were carried out with suspensions of the test substances in 0.9% sodium chloride. 0.18 ml of citrate plasma was treated with a 10 μl suspension of the test compounds and incubated at 37° C. for 10 minutes, whereupon the aggregation was initiated by the addition of 10 μl of a suspension of collagen fibrils. An $EC_{50}$ value of 6.5 μM was found with 7-dimethylamino-4,5-dihydroimidazo[1,2-a]quinazolin-2(1H)-one hydrochloride.

The experimental procedure described hereinafter was used to determine the gastric acid secretion-inhibiting activity. The pylorus of female rats, which had received no food for 24 hours, but which had received water ad libitum, is ligatured under slight ether narcosis in accordance with Shay et al (Gastroenterology, 5, 1945, 43). Immediately thereafter the substance to be tested is administered intraduodenally to the animals. Four hours later the animals are killed, the volume and the acidity of their gastric juice are determined and the values obtained are compared with those of control animals which were treated similarly, but which received no test substance. The ED 50 is that dosage of test substance which brings about a 50% decrease in volume (ED 50 volume) or acidity (ED 50 acidity) of the gastric juice in the treated animals in comparison with the control animals. The following values were found for 7-dimethylamino-4,5-dihydroimidazo[1,2-a]quinazolin-2(1H)-one hydrochloride: ED 50 volume=90 mg/kg i.d. and ED 50 acidity=65 mg/kg i.d.

The positive inotropic activity was measured after the oral administration of the test substances to conscious sheepdogs. For this purpose, the animals are provided with an implanted pressure-telemetry system, whereby the pressure receiver is fixed in the left ventricle. The left ventricular pressure is sent from the animal via the implanted radio transmitter and received via a suitable antenna and receiver system, demodulated and amplified. By differentiation of the ascending side of the left ventricular pressure (LVP) there is calculated the maximum pressure rate increase ($dLVP/dt_{max}$) which represents the contractility parameter. Simultaneously, the heart rate is recorded via a cardiotachograph. The percentage variation (Δ%) of $dLVP/dt_{max}$ and the duration of activity in hours (hrs.) are set out under inotropy. For 7-dimethylamino-4,5-dihydroimidazo [1,2-a]quinazolin-2(1H)-one hydrochloride at a dosage of 10 mg/kg there were established a positive inotropic activity (Δ=+50%, 6 hrs.) without substantial tachycardia (Δ=+36%, 6 hrs.).

The Examples which follows further illustrate the invention. All temperatures are in degrees Centigrade unless otherwise stated.

EXAMPLE 1

Preparation of 7-dimethylamino-4,5-dihydroimidazoll,2-alquinazolin-2(1H)-one

A solution of 7 g of 7-dimethylamino-4,5-dihydro-4-(p-methoxybenzyl)-imidazo[1,2-a]quinazolin-2(1H)-one in 200 ml of 85% phosphoric acid and 10 ml of anisole was stirred at 135° for 24 hours. After cooling, the mixture was adjusted to pH 9 with potassium hydroxide and the product was filtered. The product, 7-dimethylamino-4,5-dihydroimidazo[1,2-a]quinazolin-2(1H)-one, was then recrystallized from a mixture of aqueous hydrochloric acid and ethanol and was isolated as the dihydrochloride monohydrate of melting point 268° (decomposition).

The quinazoline starting material can be prepared as follows (a) A solution of 189 g of 5-dimethylamino-2-nitrobenzoic acid in 1.5 l of 1,2-dimethoxyethane was treated with 52 g of sodium borohydride and then dropwise at 10° with a solution of 225 ml of boron trifluoride etherate in 500 ml of 1,2-dimethoxyethane. The mixture was then stirred at room temperature for 1 hour, cautiously poured into ice/water and the crude product was filtered. Recrystallization from ethyl acetate/hexane gave pure 5-dimethylamino-2-nitrobenzyl alcohol, m.p. 138°–139°.

(b) A suspension of 78 g of 5-dimethylamino-2-nitrobenzyl alcohol in 80 ml of dimethylformamide and 1 l of ether was treated dropwise at 10° with 60 ml of thionyl chloride. After 4 hours at 10°, the mixture was poured into water, carefully neutralllized with sodium bicarbonate and extracted with ethyl acetate. After evaporation of the ethyl acetate, the residue was digested in cold methanol and filtered. The yield of α-chloro-N,N-dimethyl-4-nitro-o-toluidine was 84 g; m.p. 120° (decomposition).

(c) A solution of 79 g of α-chloro-N,N-dimethyl-4-nitro-o-toluidine in 1.2 l of ethanol was treated with 100 ml of 4-methoxybenzylamine and 140 ml of triethylamine and boiled under reflux for 4 hours. The solvent was then evaporated, the residue was suspended in 10% sodium carbonate solution and extracted with ethyl acetate. After evaporation, the residue was crystallized from ethyl acetate/hexane. The melting point of the pure 3-dimethylamino-4'-methoxy-6-nitro-dibenzylamine was 82°–83°.

(d) A solution of 77 g of 3-dimethylamino-4'-methoxy-6-nitro-dibenzylamine in 1100 ml of ethanol and 70 ml of triethylamine was hydrogenated in the presence of Raney-nickel. After filtration and evaporation, the product, 3-dimethylamino-4'-methoxy-6-aminodibenzylamine, was obtained as an oil.

(e) A solution of 63 g of 3-dimethylamino-4'-methoxy-6-amino-dibenzylamine in 900 ml of dioxane was treated with 23.5 g of cyanogen bromide and the mixture was stirred at room temperature for 20 hours. 150 ml of diethyl ether were then added thereto. The solution was boiled under reflux for 4 hours. After cooling, the solution was decanted from the solid crude product and the latter was recrystallized from methanol. There were obtained 32 g of 2-amino-6-dimethylamino-3,4-dihydro-3-(p-methoxybenzyl)-quinazoline, m.p. 175°–180° (as the hydrobromide).

(f) A solution of 19.5 g of 2-amino-6-dimethylamino-3,4-dihydro-3-(p-methoxybenzyl)-quinazoline in 300 ml of dimethylformamide was treated with 90 g of potassium carbonate and 12.9 g of ethyl iodoacetate and the mixture was stirred at room temperature for 20 hours and then at 85° for 5 hours. The mixture was then cooled, poured into ice/water and the crude product was filtered. Pure 7-dimethylamino-4,5-dihydro-4-(p-methoxybenzyl)-imidazo[1,2-a]quinazolin-2(1H)-one of melting point 196°–200° was obtained by recrystallization from methanol.

EXAMPLE 2

Preparation of
7-dimethylamino-4,5-dihydro-6-methyl-imidazo[1,2-a]quinazolin-2(1H)-one In a manner analogous to Example 1, from 7-dimethylamino-4,5-dihydro-4-(p-methoxybenzyl)-6-methylimidazo[1,2-a]quinazolin-2(1H)-one, m.p. 245°–248° (decomposition), there is obtained 7-dimethylamino-4,5-dihydro-6-methylimidazo[1,2-a]quinazolin-2(1H)-one; melting point of the dihydrochloride after crystallization from ethanol 275°–276° (decomposition).

The quinazoline starting material is prepared in a manner analogous to Example 1 from 5-dimethylamino-6-methyl-2-nitrobenzyl alcohol. The latter can be prepared as follows 1 mol of 2,6-dichloro-3-nitrotoluene in 1 l of dimethyl sulfoxide was stirred at 150° for 5 hours with 1 mol of copper (I) cyanide. The mixture was then cooled, poured into water and extracted with ethyl acetate. The organic phase was evaporated and the residue was purified by chromatography on silica gel. There was obtained 2-methyl-3-chloro-6-nitrobenzonitrile (yield 60%), m.p. 97°–98°.

142 g of the foregoing nitrile were stirred at 100° for 4 hours in 1.4 l of 80% sulfuric acid, the mixture was then cooled and poured into water, and the crude acid amide (m.p. 155°–157°) was filtered. This acid amide was dissolved in 600 ml of 60% sulfuric acid and at 90° there was added dropwise a solution of 81 g of potassium nitrite in 100 ml of water. The mixture was then cooled, diluted with water and the precipitated 3-chloro-2-methyl-6-nitrobenzoic acid, m.p. 130°–133°, was filtered.

A solution of 171 g of the foregoing acid in 1 l of 30% methanolic dimethylamine was stirred at 100° in an autoclave for 20 hours. The mixture was then cooled, poured into water, acidified with acetic acid and extracted with ethyl acetate. The organic phase was evaporated. The crude, partly solid 2-nitro-5-dimethylamino-6-methylbenzoic acid (143 g) was dissolved in 1.5 ml of monoglyme and the solution was treated with 33.4 g of sodium borohydride. 143 ml of boron trifluoride etherate were then added dropwise to the mixture and the resulting mixture was stirred for 20 hours. The mixture was then evaporated, diluted with water and extracted with ethyl acetate. The organic phase was dried, evaporated and chromatographed on a silica gel column.

46 g of pure 2-nitro-5-dimethylamino-6-methylbenzyl alcohol, mp. 42°–43°, were obtained by recrystallization from ether/hexane.

EXAMPLE 3

In a manner analogous to Example 1, from 6-dimethylamino-4-(p-methoxybenzyl)-4,5-dihydroimidazo[1,2-a]quinazolin-2(1H)-one, m.p. 159°–160° (decomposition), there is obtained 6-dimethylamino-4,5-dihydroimidazo[1,2-a]quinazolin-2(1H)-one, m.p. 220°–225° (decomposition).

EXAMPLE 4

In a manner analogous to Example 1, from 6-dimethylamino-1-methyl-4-(p-methoxybenzyl)-4,5-dihydroimidazo[1,2-a]quinazolin-2(1H)-one there is obtained 6-dimethylamino-1-methyl-4,5-dihydroimidazo[1,2-a]quinazolin-2(1H)-one.

EXAMPLE 5

In a manner analogous to Example 1, from 6-dimethylamino-7-methyl-4-(p-methoxybenzyl)-4,5-dihydroimidazo[1,2-a]quinazolin-2(1H)-one there is obtained 6-dimethylamino-7-methyl-4,5-dihydroimidazo[1,2-a]quinazolin-2(1H)-one.

EXAMPLE 6

In a manner analogous to Example 1, from 7-chloro-6-dimethylamino-4-(p-methoxybenzyl)-4,5-dihydroimidazo[1,2-a]quinazolin-2(1H)-one there is obtained 7-chloro-6-dimethylamino-4,5-dihydroimidazo[1,2-a]quinazolin-2(1H)-one.

EXAMPLE 7

In a manner analogous to Example 1, from 6-dimethylamino-7-methoxy-4-(p-methoxybenzyl)-4,5-dihydroimidazo[1,2-a]quinazolin-2(1H)-one there is obtained 6-dimethylamino-7-methoxy-4,5-dihydroimidazo[1,2-a]quinazolin-2(1H)-one.

EXAMPLE 8

In a manner analogous to Example 1, from 6-chloro-7-dimethylamino-4-(p-methoxybenzyl)-4,5-dihydroimidazo[1,2-a]quinazolin-2(1H)-one there is obtained 6-chloro-7-dimethylamino-4,5-dihydroimidazo[1,2-a]quinazolin-2(1H)-one.

EXAMPLE 9

In a manner analogous to Example 1, from 7-dimethylamino-1-methyl-4-(p-methoxybenzyl)-4,5-dihydroimidazo[1,2-a]quinazolin-2(1H)-one there is obtained 7-dimethylamino-1-methyl-4,5-dihydroimidazo[1,2-a]quinazolin-2(1H)-one.

EXAMPLE 10

In a manner analogous to Example 1, from 6-chloro-7-dimethylamino-1-methyl-4-(p-methoxybenzyl)-4,5-dihydroimidazo[1,2-a]quinazolin-2(1H)-one there is obtained 6-chloro-7-dimethylamino-1-methyl-4,5-dihydroimidazo[1,2-a]quinazolin-2(1H)-one.

EXAMPLE 11

In a manner analogous to Example 1, from 7-dimethylamino-4,5-dihydro-4-(p-methoxybenzyl)-1,6-dimethylimidazo[1,2-a]quinazolin-2(1H)-one, m.p. 201°–206°, there is obtained 7-dimethylamino-4,5-dihydro-1,6-dimethylimidazo[1,2-a]quinazolin-2(1H)-one, m.p. 255°–257° (decomposition).

EXAMPLE 12

Tablets of the following composition are produced in the usual manner:

| | |
|---|---|
| 7-Dimethylamino-4,5-dihydroimidazo[1,2-a]-quinazolin-2(1H)-one hydrochloride | 185.0 mg |
| Lactose | 15.0 mg |
| Maize starch | 37.5 mg |
| Water-soluble polyvinylpyrrolidone | 10.0 mg |
| Magnesium stearate | 2.5 mg |
| Total weight per tablet | 250.0 mg |

EXAMPLE 13

Interlocking gelatine capsules containing the following ingredients are produced in the usual manner:

| | |
|---|---|
| 7-Dimethylamino-4,5-dihydroimidazo[1,2-a]-quinazolin-2(1H)-one hydrochloride | 200.0 mg |
| Water-soluble polyvinylpyrrolidone | 2.0 mg |
| Maize starch | 43.0 mg |
| Talc | 4.5 mg |
| Magnesium stearate | 0.5 mg |
| Total weight per capsule | 250.0 mg |

EXAMPLE 14

An injection solution of the following composition is produced in the usual manner:

| | |
|---|---|
| 7-Dimethylamino-4,5-dihydroimidazo[1,2-a]-quinazolin-2(1H)-one hydrochloride | 115.0 mg |
| Glycerinformal | 2.4 ml |
| Water | 4.0 ml |

What is claimed is:

1. A compound of the formula

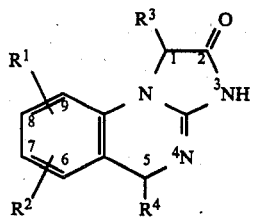

wherein one of $R^1$ or $R^2$ is hydrogen, chlorine, bromine, $C_{1-4}$-n-alkyl or $C_{1-4}$-n-alkoxy and the other is —N(R,R″), wherein R and R″ are $C_{1-4}$-n-alkyl or R and R″ taken together are tetramethylene or pentamethylene, and $R^3$ and $R^4$, independently, are hydrogen or methyl,
a tautomer thereof, when $R^3$ and/or $R^4$ are other than hydrogen, an enantiomer thereof, or a physiologically compatible acid addition salt thereof.

2. A compound in accordance with claim 1, wherein one of $R^1$ or $R^2$ is hydrogen, chlorine or bromine and the other is —N(R,R″).

3. A compound in accordance with claim 2, wherein the group —N(R,R″) is located in the 6- or 7-position.

4. A compounds in accordance with claim 3, wherein R and R″ is $C_{1-4}$-n-alkyl.

5. A compound in accordance with claim 4, wherein $R^3$ and $R^4$ is hydrogen.

6. A compound in accordance with claim 1, 7-dimethylamino-4,5-dihydroimidazo[1,2-a]quinazolin-2(1H)-one, its tautomers or enantiomers, as well as physiologically compatible acid addition salts thereof.

7. A compound in accordance with claim 1,

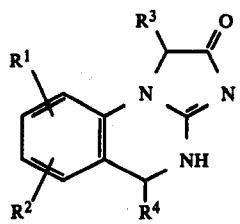

wherein one of $R^1$ or $R^2$ is hydrogen, chlorine, bromine, $C_{1-4}$-n-alkyl or $C_{1-4}$-n-alkoxy and the other is —N(R,R″), wherein R and R″ are $C_{1-4}$-n-alkyl or R and R″ taken together are tetramethylene or pentamenthylene, and $R^3$ and $R^4$, independently, are hydrogen or methyl,
and, when $R^3$ and/or $R^4$ are other than hydrogen, an enantiomer thereof, as well as a physiologically compatible acid addition salt thereof.

8. A compound in accordance with claim 1,

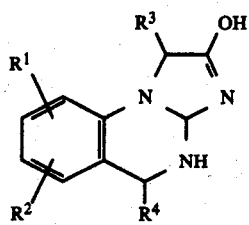

wherein one of $R^1$ or $R^2$ is hydrogen, chlorine, bromine, $C_{1-4}$-n-alkyl or $C_{1-4}$-n-alkoxy and the other is —N(R,R″), wherein R and R″ are $C_{1-4}$-n-alkyl or R and R″ taken together are tetramethylene or pentamethylene, and $R^3$ and $R^4$, independently, are hydrogen or methyl,
and, when $R^3$ and/or $R^4$ are different, an enantiomer thereof, as well as a physiologically compatible acid addition salt thereof.

9. A pharmaceutical composition for preventing thrombosis comprising an effective amount of a compound of the formula

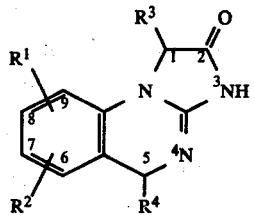

wherein one of $R^1$ or $R^2$ is hydrogen, chlorine, bromine, $C_{1-4}$-n-alkyl or $C_{1-4}$-n-alkoxy and the other is —N(R,R″), wherein R and R″ are $C_{1-4}$-n-alkyl or R and R″ taken together are tetramethylene or pentamethylene, and $R^3$ and $R^4$, independently, are hydrogen or methyl,
a tautomer thereof, where $R^3$ and/or $R^4$ are other than hydrogen, an enantiomer thereof, or a physiologically compatible acid addition salt of such a compound, and an inert pharmaceutical carrier.

10. A method of treating or preventing cardiac insufficiency which comprises administering an effective amount of a compound of the formula

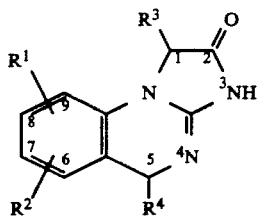

wherein one of $R^1$ or $R^2$ is hydrogen, chlorine, bromine, $C_{1-4}$-n-alkyl or $C_{1-4}$-n-alkoxy and the other is —N(R,R''), wherein R and R'' are $C_{1-4}$-n-alkyl or R and R'' taken together are tetramethylene or pentamethylene, and $R^3$ and $R^4$, independently, are hydrogen or methyl, a tautomer thereof, when $R^3$ and/or $R^4$ are other than hydrogen, an enantiomer thereof, or a physiologically compatible acid addition salt thereof.

11. A method of preventing thromboses which comprises administering an effective amount of a compound of the formula

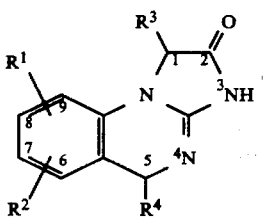

wherein one of $R^1$ or $R^2$ is hydrogen, chlorine, bromine, $C_{1-4}$-n-alkyl or $C_{1-4}$-n-alkoxy and the other is —N(R,R''), wherein R and R'' are $C_{1-4}$-n-alkyl or R and R'' taken together are tetramethylene or pentamethylene, and $R^3$ and $R^4$, independently, are hydrogen or methyl, a tautomer thereof, when $R^3$ and/or $R^4$ are other than hydrogen, an enantiomer thereof, or a physiologically compatible acid addition salt thereof.

12. A method of treating gastric ulcers which comprises administering an effective amount of a compound of the formula

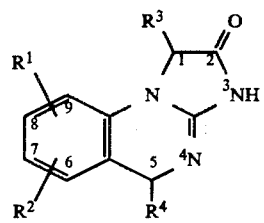

wherein one of $R^1$ or $R^2$ is hydrogen, chlorine, bromine, $C_{1-4}$-n-alkyl or $C_{1-4}$-n-alkoxy and the other is —N(R,R''), wherein R and R'' are $C_{1-4}$-n-alkyl or R and R'' taken together are tetramethylene or pentamethylene, and $R^3$ and $R^4$, independently, are hydrogen or methyl, a tautomer thereof, when $R^3$ and/or $R^4$ are other than hydrogen, an enantiomer thereof, or a physiologically compatible acid addition salt thereof.

13. A pharmaceutical composition for treating gastric ulcers comprising an effective amount of a compound of the formula

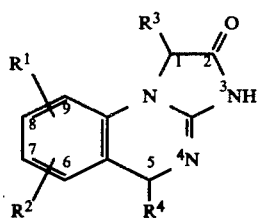

wherein one of $R^1$ or $R^2$ is hydrogen, chlorine, bromine, $C_{1-4}$-n-alkyl or $C_{1-4}$-n-alkoxy and the other is —N(R,R''), wherein R and R'' are $C_{1-4}$-n-alkyl or R and R'' taken together are tetramethylene or pentamethylene, and $R^3$ and $R^4$, independently, are hydrogen or methyl, a tautomer thereof, where $R^3$ and/or $R^4$ are other than hydrogen, an enantiomer thereof, or a physiologically compatible acid addition salt of such a compound, and an inert pharmaceutical carrier.

14. A pharmaceutical composition for the treating of cardiac insufficiency comprising an effective amount of a compound of the formula

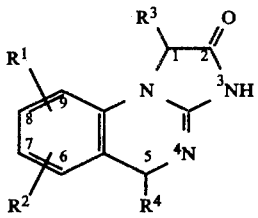

wherein one of $R^1$ or $R^2$ is hydrogen, chlorine, bromine, $C_{1-4}$-n-alkyl or $C_{1-4}$-n-alkoxy and the other is —N(R,R''), wherein R and R'' are $C_{1-4}$-n-alkyl or R and R'' taken together are tetramethylene or pentamethylene, and $R^3$ and $R^4$, independently, are hydrogen or methyl, a tautomer thereof, where $R^3$ and/or $R^4$ are other than hydrogen, an enantiomer thereof, or a physiologically compatible acid addition salt of such a compound, and an inert pharmaceutical carrier.

* * * * *